United States Patent [19]

Strimling

[11] Patent Number: 4,512,726
[45] Date of Patent: Apr. 23, 1985

[54] PUMP ADAPTABLE FOR USE AS AN ARTIFICIAL HEART

[76] Inventor: Walter E. Strimling, 63 Westcliff Rd., Weston, Mass. 02193

[21] Appl. No.: 347,184

[22] Filed: Feb. 9, 1982

[51] Int. Cl.³ .................. F04B 43/04; A61F 1/00; A61M 1/03
[52] U.S. Cl. ................... 417/412; 417/475; 3/1.7; 128/DIG. 3; 128/1 D
[58] Field of Search .............. 417/413, 475, 412, 418, 417/410; 3/1.7; 128/DIG. 3, 1 D

[56] References Cited

U.S. PATENT DOCUMENTS

| | | | |
|---|---|---|---|
| 922,205 | 5/1909 | Still | 417/475 |
| 2,818,815 | 1/1958 | Corneil | 417/475 |
| 3,046,903 | 6/1962 | Jones | 417/475 |
| 3,152,340 | 10/1964 | Fry et al. | 3/1.7 |
| 3,411,704 | 11/1968 | Hilgert et al. | 417/413 |
| 3,486,099 | 12/1969 | Brunner et al. | 310/10 |
| 3,496,874 | 2/1970 | Findlay | 128/DIG. 3 |
| 3,514,218 | 5/1970 | Maher, Jr. | 417/418 X |
| 3,515,966 | 6/1970 | Valroger et al. | 417/413 |
| 3,522,494 | 8/1970 | Bosch | 310/10 |
| 3,541,361 | 11/1970 | Nola | 310/10 |
| 3,720,485 | 3/1973 | Holman, Jr. | 417/413 |
| 3,842,440 | 10/1974 | Karlson | 417/412 X |
| 4,058,857 | 11/1977 | Runge et al. | 412/412 X |

FOREIGN PATENT DOCUMENTS

| | | | |
|---|---|---|---|
| 1051595 | 2/1959 | Fed. Rep. of Germany | 417/413 |
| 425510 | 10/1947 | Italy | 417/475 |

OTHER PUBLICATIONS

Poirier et al, "Development of Electrical Energy Converters To Power and Control Left Heart Assist Devices," National Heart, Lung, and Blood Institute Tech. Report, No. N01-HV-7-2976-2, Jun. 1979.

*Primary Examiner*—Carlton R. Croyle
*Assistant Examiner*—Paul F. Neils
*Attorney, Agent, or Firm*—Bromberg, Sunstein & McGregor

[57] ABSTRACT

A pump adaptable for use as a human heart includes first and third pump chambers separated from an intermediate second chamber which may house a motor. The chambers are separated by diaphragms which may be alternately driven. A pump is achieved which needs no venting. Each of the first and third chambers can pump blood in operation and can be connected in series or separately to the ventricles of the heart.

9 Claims, 14 Drawing Figures

PUMP ADAPTABLE FOR USE AS AN ARTIFICIAL HEART

DESCRIPTION

1. Field of the Invention

This invention relates to fluid pumps and more particularly to such pumps adaptable for use as a human heart.

2. Background of the Invention

Pumps of all types are familiar in the art. One common type of pump includes a diaphragm operative to divide an enclosed volume into first and second chambers. Reciprocal movement of the diaphragm along an axis normal to the diaphragm alternately expands and reduces the volume of the first chamber at the expense of the second. Suitable inlet and outlet conduits and check valves allow fluids first to be drawn into the first chamber and then to be expelled. Frequently, electromagnetic means provide the requisite movement of the diaphragm.

The problem with such pumps is that a fluid medium is required in the second chamber in order to enable the pump to operate satisfactorily. But such a medium has to be vented thus excluding the use of such pumps in, say, the hostile environment of space, or in submersible applications or as a human heart implant.

My copending application Ser. No. 257,752 filed Apr. 27, 1981 disclosed a pump arrangement wherein the need for venting a pump is obviated by including the same medium in each of the two chambers into which a pump is divided. In addition, the two chambers expand and contract at the expense of one another to produce two pumping actions during each cycle of operation. Although such an arrangement is attractive and facilitates solutions to such basic problems as fluid contamination and diaphragm fracture as well as to the venting problem, the use of the pump as a heart assist or heart replacement requires components which are larger and heavier than are desirable for use in a human body.

Consequently, the problems which the present invention addresses are related to a reduction in the size and weight, and an increase in the efficiency of a pump particularly adapted for use as a heart assist or replacement.

BRIEF DESCRIPTION OF THE INVENTION

The foregoing problems are resolved in accordance with this invention by a pump which is divided into three chambers which can be visualized as aligned along an axis. The first and third chambers expand and contract alternately whereas the second chamber is adapted to displace its position along the axis towards the chamber which is contracting. The second chamber is separated from the first and third chambers by moving members such as diaphragms which move in concert. The pump exhibits all the advantages described in my above-identified copending application.

In a preferred embodiment, the drive arrangement for the moving members is housed within the second chamber in a manner to permit highly efficient use of space.

DETAILED DESCRIPTION

Figure 1:
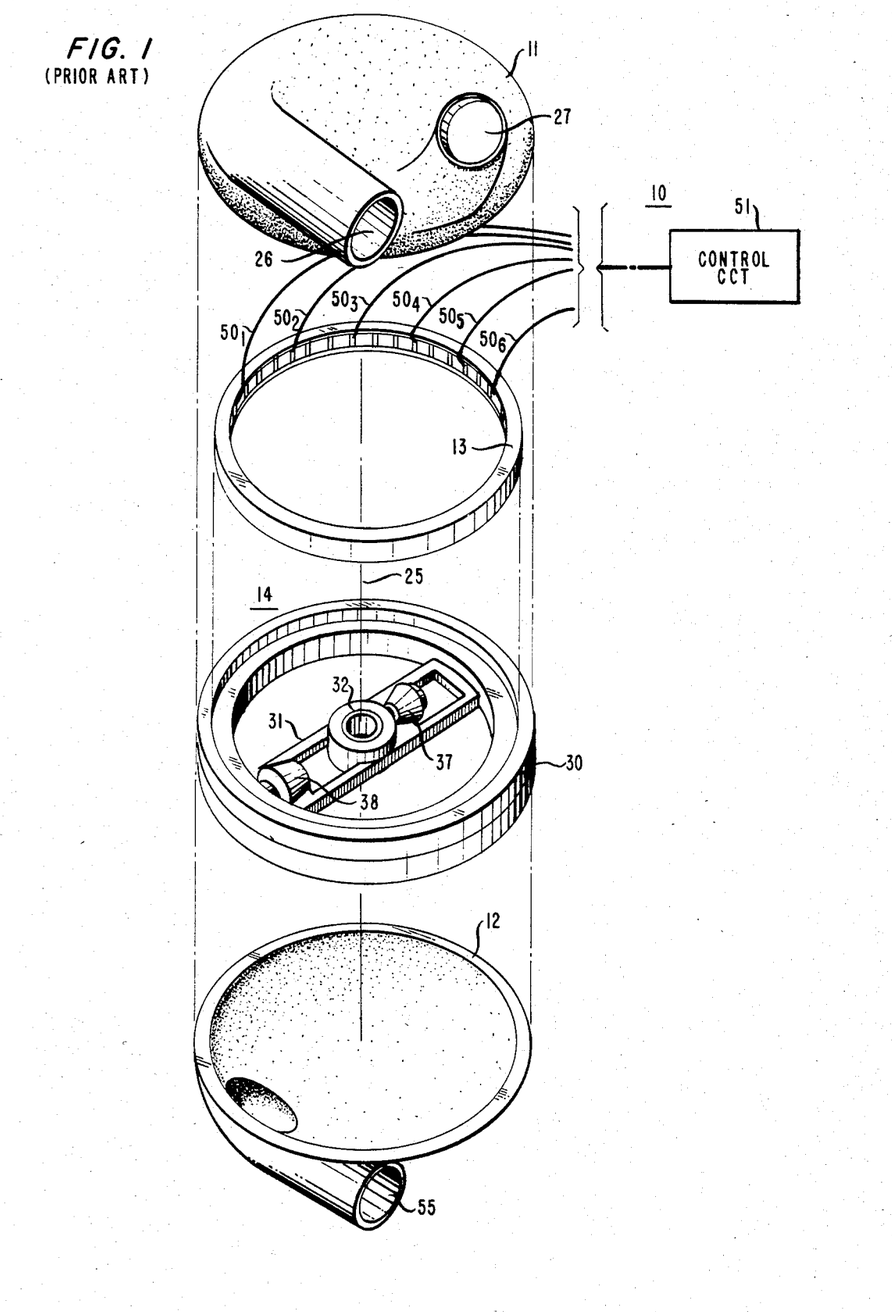
FIGS. 1 and 5 are exploded views of a prior art pump arrangement and a pump arrangement in accordance with an embodiment of this invention.

FIG. 1 shows an exploded view of a prior art pump arrangement 10 suitable for use as an artificial heart. The pump arrangement comprises four subassemblies: top and bottom cover plate assemblies 11 and 12 respectively, and a commutatorless stator 13 with mating rotor assembly 14. The four subassemblies are connected at their peripheries to form a pancake-type motor assembly.

Figure 2:
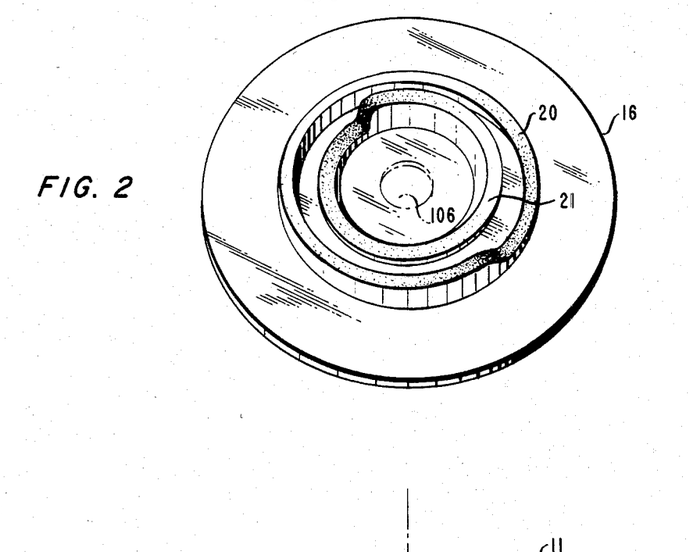
FIGS. 2 and 3 are top and side views of portions of the pump arrangement of FIG. 1.
Figure 3:
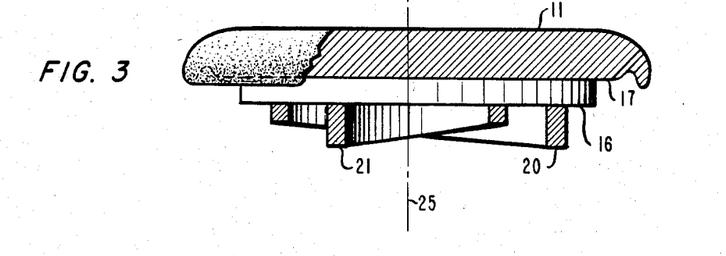

The top cover plate forms a first chamber with a cam pusher plate 16 shown in FIG. 2. Plate 16 has concentric cams or ramps 20 and 21 affixed to it. Plate 16 presses against a flexible diaphragm 17 which is sealed at its circumference to top cover plate 11 as shown in FIG. 3. In operation plate 16 moves upward as viewed in FIG. 3 along axis 25 so that the volume of the chamber defined between plate 16 and cover plate 11 contracts. Any fluid in the chamber thus can be made to exit conduit 27 of FIG. 1. Normal body blood pressure causes the chamber to expand thereafter with blood entering the chamber through conduit 26. The conduits include appropriate check valves as will be discussed more fully hereinafter.

Figure 4:
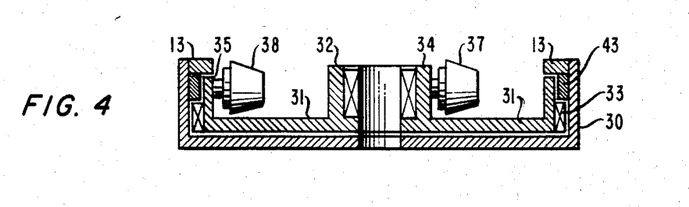
FIG. 4 is a cross sectional view of a portion of the pump arrangement of FIG. 1.

The upward movement of plate 16 is achieved by means of the commutatorless stator 13 and mating rotor assembly 14. Assembly 14 comprises a cup-shaped housing 30 shown in cross section in FIG. 4. The assembly also includes cross brace 31 with raised central bearing portion 32 on which plate 16 of FIG. 2 rests. Annular ring 33, of magnetic material, fits within the periphery of housing 30 as shown in FIG. 4. Ring 33 includes a plurality of magnetic sections of samarium cobalt, the periphery of which forms eleven salient pole pairs that define the inner radius of the torque motor air gap and provide the operating flux as described more fully hereinafter. Cross brace 31 includes interior and exterior vertical wall 34 and 35 respectively to which wheels 37 and 38 are affixed as is also shown in FIG. 4. Wheels 37 and 38 are positioned to bear against cams 21 and 20 of FIG. 2 respectively. Exterior wall 35 is secured to magnetic ring 33.

In operation, rotor assembly 14 rotates ring 33 causing wheels 37 and 38 to bear against cams 21 and 20 in a manner to cause upward movement of plate 16 of FIG. 2. The rotation of magnetic ring 33 occurs in response to current pulses applied to consecutive windings of stator 13. To this end, assembly 14 includes a side keeper 43 of FIG. 4 secured to housing 30. Stator 13 fits within keeper 43 as shown in FIG. 4. Stator 13 includes a winding arrangement with six separate leads. The leads are designated $50_1, 50_2, 50_3, \ldots 50_6$ in FIG. 1 and are connected between a control circuit, represented by block 51 in FIG. 1, and ground. Control circuit 51 pulses the leads in sequence generating current flow in consecutive sections of stator 13 causing a succession of magnetic fields around the periphery of magnetic ring 33. In turn, movement of the ring and cross brace results. It should be clear at this juncture in the description that the rotation of ring 33 causes plate 16 of FIG. 2 to move upward causing the volume changes in the first chamber as described.

Plate 12 of FIG. 1 includes an aperture 55 for venting the pump arrangement to the exterior of the body.

Figure 5:
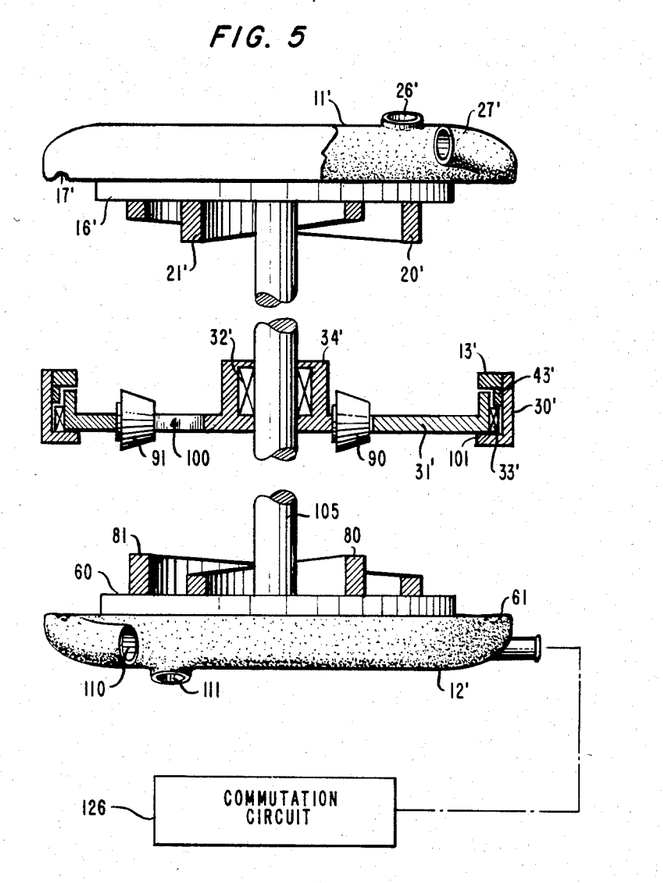

FIG. 5 shows a pump arrangement in accordance with this invention. For ease of comparison between the embodiments of FIGS. 1 to 4, and FIG. 5, numbers used to designate elements in the embodiment of FIGS. 1 to 4 are used with prime indications to designate like elements in the embodiment of FIG. 5. The arrangement includes a lower pusher plate 60 in addition to upper pusher plate 16'. Pusher plate 60 includes the ramps designated 80 and 81 in the figure and adapted to bear against wheels 90 and 91 respectively. Wheels 90 and 91 correspond to wheels 37 and 38 of FIG. 4. Pusher plate 60 presses against a flexible diaphragm 61 which is sealed at its circumference to cover plate 12' in this embodiment. As can be seen in FIG. 5, wheels 90 and 91 are recessed into apertures in cross brace 31' so that the wheels can contact all of ramps 20', 21', 80 and 81. In this manner, the movements of diaphragms 17' and 61 are alternately driven in the manner discussed below.

In the embodiment of FIG. 5, cross brace 31' housing 30' are apertured to permit wheels 90 and 91 to protrude below cross brace 31' to make contact with ramps 80 and 81. The aperture is designated 100 in FIG. 5. The remaining portion of housing 30' provides a bearing surface 101 in which cross brace 31' rotates.

In operation, the rotation of cross brace 31' drives wheels 90 and 91 against ramps 20', 21' 80 and 81 in a manner to expand the chamber between cover plate 11' and diaphragm 17' while it contracts the chamber between cover plate 12' and diaphragm 61 and vice versa.

Figure 6:
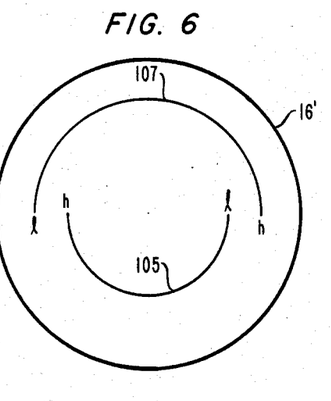
FIGS. 6 and 7 are schematic face views of portions of the pump arrangement shown in FIG. 5 as seen from the center of the pump looking up to one face and down to the other.
Figure 7:
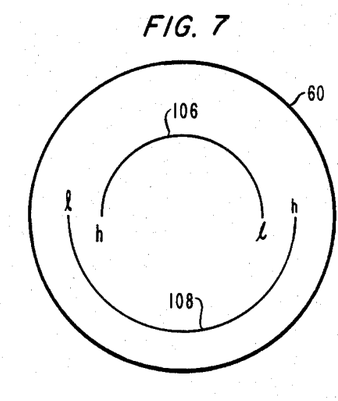

In order for the arrangement of FIG. 5 to be operative to drive both pusher plates 16' and 60, the ramps 20' and 21' and ramps 80 and 81 are mounted 180° from one another. The arrangement of ramps is shown in FIGS. 6 and 7. The ramps for wheel 90 are designated 105 and 106 in FIGS. 6 and 7 respectively. The ramps for wheel 91 are designated 107 and 108 respectively. The ends of the ramps are designated high (h) or low (l) to identify the raised and low ends respectively.

Note that the chamber between cover plate 12' and diaphragm 61 includes entrance and exit conduits 111 and 110 which are not present in the prior art arrangement of FIG. 1.

For convenience, the chamber formed by cover plate 11' and diaphragm 17' will sometimes be referred to as the "upper pump chamber" and the chamber formed by cover plate 12' and diaphragm 61 will sometimes be referred to as the "lower pump chamber". The chamber included between the diaphragms 17' and 61 will sometimes be referred to as the "middle chamber". It will be apparent that the total volume included in the upper pump chamber, lower pump chamber, and middle chamber is constant in the embodiments herein described, since these three chambers include substantially the total volume within what amounts to a housing of fixed dimension.

In one embodiment of the invention, pusher plates 16' and 60 are connected by a rod 105 as shown in FIG. 5. The rod is secured to each plate at a position indicated at 106 in FIG. 2. If the pusher plates are secured to the diaphragms (or pistons) in this embodiment, it is clear that the upper and lower chambers expand and contract at the expense of one another thus maintaining a constant total volume in those two chambers.

Figure 5A:
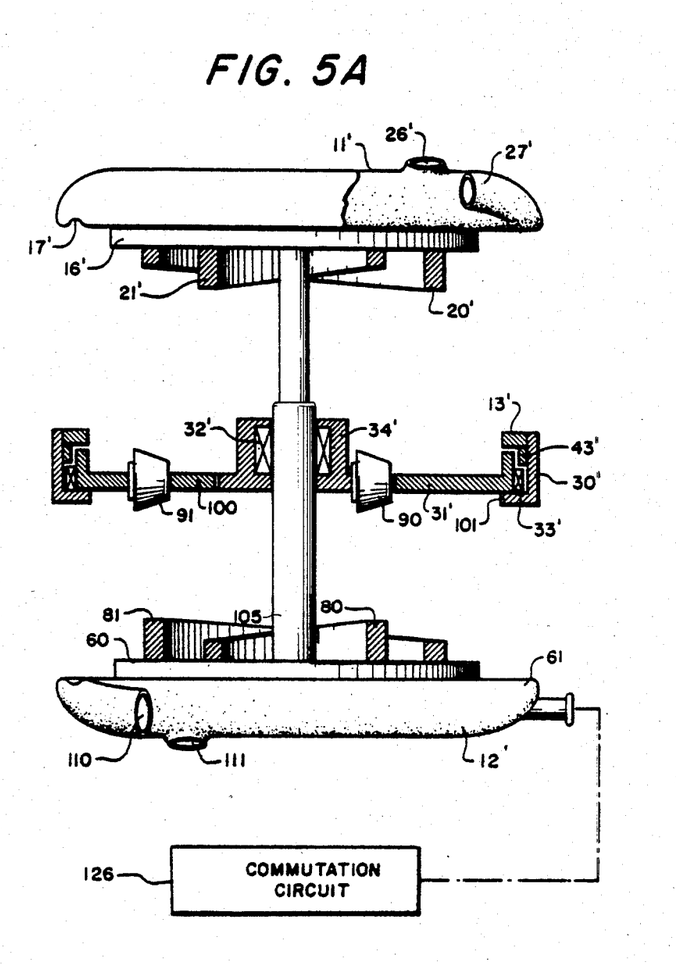
FIG. 5a shows a pump according to the present invention with variable length guide means.

In a second embodiment, rod 105 shown in FIG. 5a is replaced by two concentric or effectively similar complimentary rods which are attached one to each pusher plate, for alignment purposes, and which slip freely, allowing rod 105 to have a variable length. Pusher plates 16' and 60 may have no attachment to diaphragms 17' and 61 and be able to retract without pulling the diaphragms which they had previously pushed. For this second embodiment it is clear that the upper and lower pump chambers contract alternately and expand alternately but do not necessarily maintain a constant total volume.

In the case of the second embodiment (in contrast to the first embodiment), when one pump chamber is undergoing a contraction caused by forces exerted by its pusher plate, the other chamber is *not* subjected to a correspondingly large expansion force by its pusher plate. Accordingly, when this embodiment is used as a heart assist or partial or total heart replacement, it may be configured so that each pump chamber during its time of expansion exerts only a small fraction, if any, of the vacuum forces in the incoming blood fluid in comparison to the vacuum forces that might be present if the first embodiment were used. In this manner, the delicate veinal system can be protected from destructive forces.

The characteristics of these embodiments are affected by the relative volume of each pump chamber in relation to the total volume of the two pump chambers together with that of the middle chamber. For example, in the first embodiment, when the upper chamber has just been subjected to its maximum compression via its pusher plate, it is at its minimum volume; when its pusher plate thereupon pulls on its diaphragm, a large suction may result from this force acting on such a small volume. In contrast, in the second embodiment, consider the corresponding situation immediately after the upper chamber has reached its minimum volume; when the upper pusher plate retracts, it does not pull on the upper diaphragm. Rather, the only force exerted on the upper diaphragm by the drive assembly is that attributable to the reduction in pressure in the middle chamber resulting from its relatively slight enlargement as the lower pusher plate presses against the lower diaphragm. If the upper diaphragm has not yet moved from its position of maximum displacement away from the lower chamber, or if the upper diaphragm moves downward at a slower rate than the lower diaphragm, the lower pusher plate will continue to enlarge the middle chamber as it pushes on the lower diaphragm, thereby causing further slight reduction in pressure of the middle chamber, and corresponding force changes on the upper diaphragm. In this manner, the second embodiment has the gentle behavior previously described. It should be noted that either embodiment will still be operative if the middle chamber is vented or connected to a variable volume compliance chamber. In the second embodiment, under such circumstances, the potential suction forces may thereby be further reduced if desired.

The overall organization of the pump arrangement of FIG. 5 and its operation as well as its volume characteristics have now been described. We will now turn our attention to the motor and its control in the embodiment of FIG. 5. The embodiment of FIG. 1 is described in terms of an existing pump arrangement produced by Thermo Electron Corporation of Waltham, Mass. and is disclosed in a report entitled "Development of Electrical Energy Converters to Power and Control Left Heart Assist Devices". The report was prepared for the Device and Technology Branch, Division of Heart and Vascular Diseases of the National Heart, Lung and Blood Institute, Bethesda, Md. 20014 (Report No. NO1-HV-7-2976-2) and is dated June 1979. The report describes the motor as comprising a stator and rotor. The stator (13) is described as including six leads which are driven in alternate pairs by an electronic commutator.

The motor is described in that report as an integral assembly of five components shown in FIG. 4. The first component is the magnet array of the commutator (ring 33) composed of twenty two samarian cobalt magnets. The second component is a vanadium permendur yoke (keeper 43) which supports the magnet assembly and provides a low-reluctance magnetic path behind adjacent magnetic pole pieces for completing the magnetic circuit which comprises the magnet, air gap, and stator core. The third component is a titanium hub (cross brace 31) which supports the magnet and yoke assemblies and provides a journal for the center bearings as well as a rigid mounting surface for the follower bearings (wheels 37 and 38).

The remaining two components of the motor are related to the bearing and movement of the rotor. The first of these components is a central bearing portion (32 of FIG. 4 and 32' of FIG. 5). The bearing provides radial alignment for the rotor and accomodates the thrust loads of the cam and pusher plate assembly. The last component comprises the follower bearings (wheels 37 and 38 of FIG. 4 and wheels 90 and 91 of FIG. 5) that impart the linear motion to the nested helical cams of each pusher plate assembly.

Figure 8:
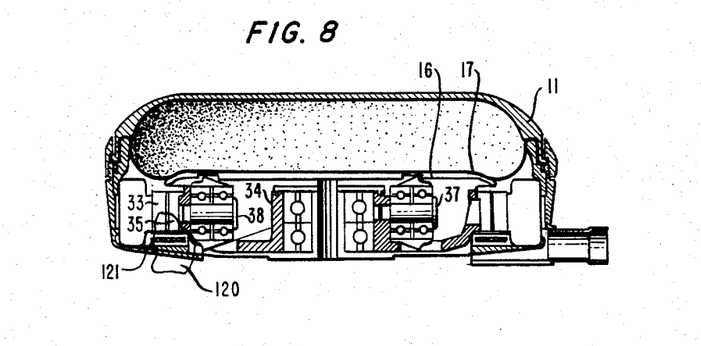
FIGS. 8 and 9 are detailed cross sections of portions of the pump arrangement shown in FIG. 1.

FIG. 8 shows a detailed cross section of these components in relation to the pusher plate and housing as they occur in the prior art arrangement. This cross sectional view would be the same for embodiments of the type shown in FIG. 5 if wheels 37 and 38 were lowered to positions shown for wheels 90 and 91 in FIG. 5.

Figure 9:
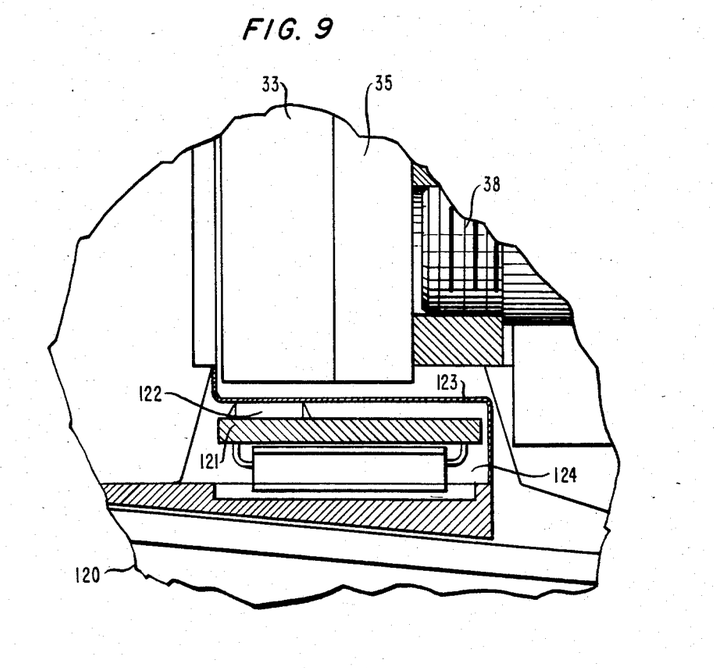

FIG. 9 shows an enlarged cross sectional view of a portion 120 of the view of FIG. 8. The figure shows a printed circuit board 121 and a Hall sensor 122 positioned within the motor housing as shown. The printed circuit board is contained within a cover plate in a volume 124 filled with potting compound. The board contains seven hybrid integrated circuit packages, two resistors and six diodes and is responsive to three Hall sensors distributed evenly around the perphery of the rotor. These elements are employed for the commutation circuitry 126 shown in FIG. 5. An eighth hybrid integrated circuit with two more Hall sensors and three more resistors is included to serve control and monitoring functions. The Hall sensors are magnetic field transducers whose differential output voltages are proportional to the intensity of an impinging magnetic field and are central to the implementation of all those functions.

ROTOR POSITION SENSING CIRCUIT

The three Hall sensors are located at the rim of the commutator ring (33) such that they fall within the fringing fields of the rotor's twenty-two magnets. The polarity of the magnets alternates, causing the Hall sensors to reverse polarity twenty-two times per revolution. The Hall devices are located in spaced apart positions equal to one third the width of the rotor. The result is that only one Hall sensor experiences a change in magnetic polarity at a time and the pattern of outputs from the three Hall sensors change sixty-six times per revolution.

Figure 10:
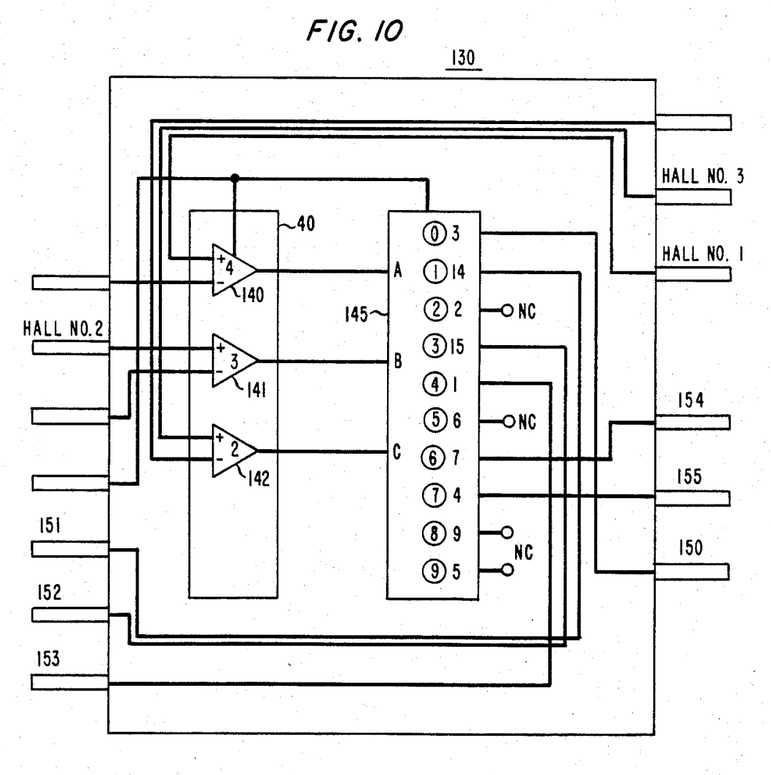
FIGS. 10 and 11 are circuit schematics of control circuitry for the pump arrangements of FIGS. 1 and 5.

FIG. 10 shows the switch logic module 130 responsive to the outputs of the Hall sensors. The module contains three comparator amplifiers 140, 141 and 142, and a three-to-eight line decoder chip 145. The outputs of the three Hall sensors are connected to inputs to comparator 140, 141, and 142 shown in the figure. The output of a comparator is high when a Hall sensor passes a north pole of the rotor. The function of an amplifier is to shape the quasi-sinesoidal voltage waveforms at the outputs of the Hall sensors to a rectified, square wave pulse compatible with CMOS (complimentary metal-oxide-semiconductor) chips as explained in the above-mentioned report.

Logic network 145 is a CMOS chip operative to translate the three-bit binary code from comparators 140, 141, 142 into a high logic level at one of eight outputs of which only six 150-155, are used. When a selected output corresponding to a three-bit code is high, the asociated one (of six) stator windings is activated in the proper polarity via the power switching circuitry shown in FIG. 11. The decoder is operative to have only one output high even in the presence of faulty or missing codes in order to avoid activating more than one winding at a time.

Figure 11:
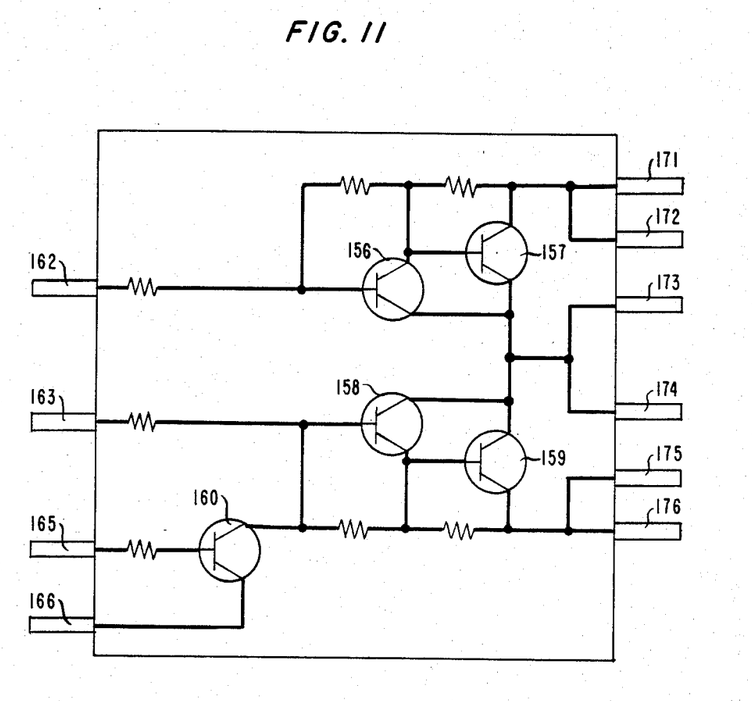

FIG. 11 shows a schematic diagram of the power switching circuitry which functions as a noncontacting analog of commutator brushes in an electrical motor. The figure shows five switches, 156, 157, 158, 159, and 160. The circuit comprises a complimentary pair of high gain Darlington powers transistors, one driven directly by the output of the circuit of FIG. 10 and one driven by a level translating and inverting circuit. The circuit includes four input leads designated 162, 163, 165, and 166 in the figure and six output leads 171, 172, 173, 174, 175, and 176 (50$_1$, 50$_2$, 50$_3$, 50$_4$, 50$_5$, and 50$_6$ of FIG. 1). Input lead 162 is connected to the base of transistor 156 and the emitter of transistor 157. The emitter of transistor 156 is connected to the base of transistor 157. The collectors of transistor 156 and 157 are connected to one another. The emitter of transistor 157 is connected to output leads 171 and 172. The collector of transistor 157 is connected to output leads 173 and 174.

The Darlington pair (158 and 159) is similarly connected between input lead 163 and the output leads with the emitter of transistor 158 connected to output leads 175 and 176 and the collector of transistor 158 connected to 173 and 174. Note that transistors 156 and 157 are NPN whereas transistors 158 and 159 are PNP. The remaining input leads 165 and 166 are connected to the base and collector of transistor 160 respectively. The emitter of transistor 160 is connected to output leads 175 and 176 as well as to the base and emitter of transistor 158. As is clear from the figure, outputs leads 171 and 172 are connected to one another. The reason for this is to handle the load. The same is true for output leads 173 and 174 as well as leads 175 and 176. Typically, leads 171 and 172 are held at a voltage of say 50 volts and leads 175 and 176 are held at ground. The output of the circuit appears on leads 173 and 174.

In operation, the output leads 173 and 174 are in one of three conditions, namely at a signal level, ground, or neither. At the input end, lead 165 is held at say plus fifty volts, and an input voltage is applied to lead 162. In response, transistors 156 and 157 turn on. A 50 volt pulse is applied to lead 166 to activate (inverter) transistor 160. In response, output leads 173 and 174 are at ground. Alternatively, the plus 50 volt signal is applied to lead 163 and the inverter, thus, is not activated. In response, leads 173 and 174 are at an output voltage level. In the third case, a plus 50 volt signal is applied to neither of leads 162 or 166 and leads 173 and 174 are floating at a high impedance.

We have now described the placement of Hall sensors in the motor housing and the implementation of commutation, control, and monitoring functions of the pumps of FIGS. 1 and 5. The above-mentioned publication supplies additional information on the implementation of such functions. The various signal pulses applied as taught herein require no changes as used in accordance with this invention.

But a pump arrangement in accordance with the present invention employs first and third chambers which fill and exhaust alternately in response to the pulses applied to the output leads shown in FIG. 11. These leads are connected to the six winding leads of stator 13' of FIG. 5, to this end. Signals applied consecutively to these leads, responsive to successive input codes on the input leads to the circuit of FIG. 10, result in an appropriate succession of fields applied to rotate ring 33' of FIG. 5. The rotor movement causes the wheels (or cam followers) to engage the cams of FIG. 6 and FIG. 7 to cause the fill and exhaust of the first and third chambers reciprocally. But the operations of the two chambers have to be coordinated.

Figure 12:
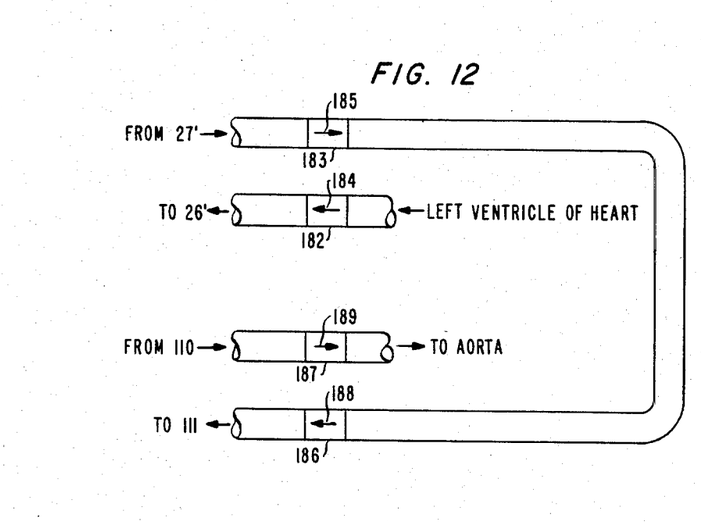
FIGS. 12 and 13 are schematic diagrams of conduit interconnections for the pump arrangement of FIG. 5.
Figure 13:
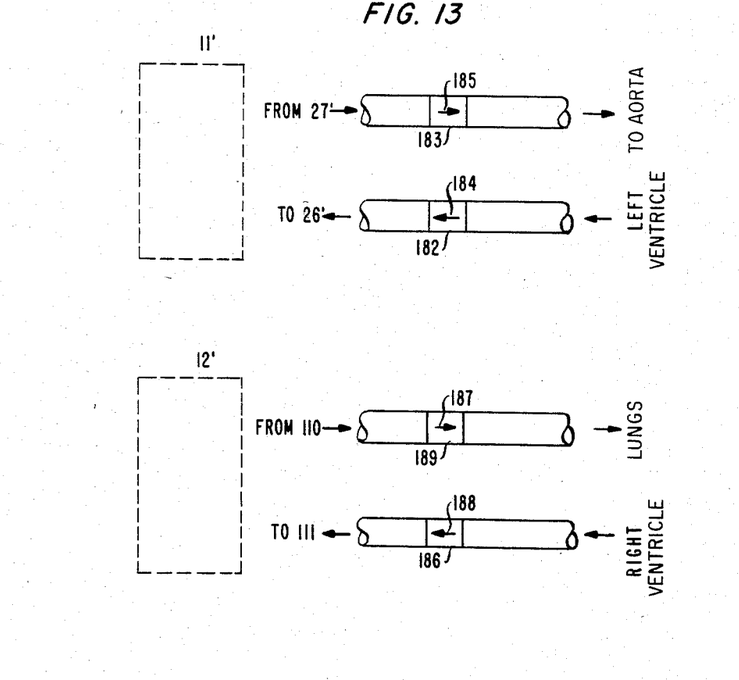

In order to coordinate the operations of the two chambers, check valves are required in the inlet and outlet conduits. In addition, the conduits may be connected so that blood passes through the first and third chambers in sequence in one embodiment and may be connected into first and second separate blood circulating paths in another. FIGS. 12 and 13 represent the modes of interconnection of the first and third chambers of FIG. 5 for implementing these two cases. We will assume that conduits 26' and 27' of FIG. 5 are entrance and exit conduits respectively of the upper chamber and that check valves 182 and 183 associated with those conduits are operative, accordingly, to allow blood to flow only as indicated by arrows 184 and 185 respectively. Similarly, check valves 186 and 187 are operative to allow blood to flow only as indicated by arrows 188 and 189 to and from entrance and exit conduits 111 and 110 respectively of the lower chamber of FIG. 5.

Case 1. Operation as a Left Ventricular Assist Device

When used as a Left Ventricular Assist Device (LVAD), the artificial heart of, for example, FIG. 5 operates with the suction side of the first pump chamber connected to an incision in the lower portion of the left ventricle of the heart. The pressure side of the first pump chamber is connected directly to the suction side of the third pump chamber, so the blood goes through both pump chambers before returning to the body. The pressure side of the third pump chamber is connected to a "Y" or a tee in the aorta. Thus the artificial heart functions in parallel with the left ventricle. This case is illustrated in FIG. 12.

A pressure or electric impulse sensor (not shown) may be used to monitor the start of contraction of the left ventricle. When the left ventricle begins to contract, the sensor triggers the circuit of FIG. 10 to cause the artificial heart to start its pressure cycle. The rotor of the pump motor then drives the pump diaphragm 61 of FIG. 5 to its full extension.

The motor speed is limited by several factors:

(a) Economy of energy consumption, torque requirements, and limitations on size and weight establish a maximum design speed of rotation.

(b) The pressure in the aorta must not exceed some safe maximum (perhaps 200 millimeters of mercury at the exit port of the artificial heart).

(c) The vacuum at the inlet port of the artificial heart must not exceed some safe maximum (perhaps 10 millimeters of mercury).

The motor speed may be programmed to insure operation within the optimum limits, or pressure sensors may be located at the inlet and outlet of the artificial heart to monitor the vacuum and pressure levels. When the vacuum level at the suction side of the artificial heart reaches approximately 8 millimeters of mercury, the motor begins to slow down in a controlled manner so as to continue its cycle smoothly without creating a vacuum exceeding 10 millimeters of mercury. Similarly, if the pressure level at the pressure side of the artificial heart reaches approximately 160 millimeters of mercury, the motor begins to slow down in a controlled manner so as to continue its cycle smoothly without creating outlet pressure exceeding 200 millimeters of mercury.

When the rotor has completed a full turn (360°) it stops. It starts again when the pressure or electric impulse sensor indicates the start of the next ventricular contraction. It continues to rotate through another full turn at its normal programmed design speed, unless the rate of rotation is reduced automatically to prevent an inlet vacuum exceeding 10 millimeters of mercury, or an outlet pressure exceeding 200 millimeters of mercury.

In lieu of, or in addition to, programming of rotor speed, the ramp design on the pusher plates may be modified. In particular, both the slope of a given ramp and the extent of its angular coverage may be varied in accordance with the desired duty cycle of each pump chamber. With appropriate design, it may possible to utilize a constant speed rotor.

If the heart stops its normal beating or if the heart is fibrillating, the monitor circuit triggers the pump rotor drive on the basis of timing. Thus, if the time required for the rotor to turn one full revolution happens to be less than some pre-set "heart-beat time", the rotor stops and waits for a signal from the heart monitor indicating the start of contraction. And if no such signal comes by the end of another pre-set time, the rotor drive starts automatically and goes through another full turn. This process repeats indefinitely.

If the time required for the rotor to turn one full revolution happens to be longer than the pre-set "heart-beat time", the rotor may be programmed to stop briefly to wait for an indication from the heart monitor of the start of the next contraction, or it may be programmed to go directly to its next revolution, depending upon which arrangement seems to be most advantageous to the patient. Circuitry for achieving such operation is well known and considered to be included in Control Circuit 51 of FIG. 1.

Case 2. Operation as a Complete Heart or Complete Heart Assist Device

When used as a complete heart or complete heart assist device, the artificial heart has its two pump chambers connected independently to the left and right ventricles separately, and/or to the appropriate blood vessels as illustrated in FIG. 13. If vacuum sensors are employed one may be located at the inlet to each pump chamber of the artificial heart. If the living heart remains also, a pressure or electric impulse sensor may be used to detect the start of a normal heart beat.

When used as a complete heart or complete heart assist device, the artificial heart operates as described in Case 1 above, except that now it operates as its normal design programmed speed subject to the limitations that neither pump chamber inlet vacuum may exceed the 10 millimeters of mercury limit, and that neither pump chamber outlet pressure may exceed the 200 millimeters of mercury limit.

The rotor rotation is controlled precisely to assure that the entire pressure and vacuum cycle is smooth and gentle. Abrupt changes in pressure and/or vacuum are to be avoided, even at start up and stop points. It is important to maintain a smooth, gentle pressure gradient at all times.

As described previously in connection with FIG. 5, in order to ensure that no excessive vacuum (in one chamber) results from a forced enlargment of that chamber from which blood has just been expelled, pusher plates 16' and 60 may be left un-attached to diaphragms 17' and 61, respectively. Body blood pressure is then the principle force causing the previously emptied chamber to refill.

Heart assist and heart replacement pumps designed in accordance with the teachings herein can be highly efficient. Not only are bulky magnets not required, but various piece parts (i.e. diaphragms) are moved relatively short distances. Consequently drive forces are relatively low. Moreover, these forces are provided by a simple electric motor which provides a single simple motion rather than a push-pull motion previously required. The simple geometry of the pump chambers, further, offers few, if any, areas in which blood can collect and coagulate during operation.

What has been disclosed is considered merely illustrative of the principle of this invention. For example, for high pressure applications, pistons rather than diaphragms would be used to advantage and it is contemplated that such alternate means for separating the various chambers herein is included within the language of the claims. Therefore, various modifications of the invention can be devised by those skilled in the art in accordance with those principles within the spirit and scope of the invention as encompassed by the following claims.

What is claimed is:

1. A pump arrangement comprising first and second pump chambers each having entrance and exit conduits, first and second means for separating said chambers and for defining an intermediate chamber therebetween, means for moving said first and second means along an axis in a manner to change the volume of said first and second pump chambers alternately, wherein said means for moving includes drive means and means proximally contactable against the first and second means for pushing said first and second means housed in said intermediate chamber, wherein the contactable means includes a pair of opposing pusher plates, each plate associated with a respective one of the first and second means, the plates having cam surfaces thereon and connected by a variable length guide means and wherein the drive means includes a rotary electric motor mounted on the guide means and having a rotor carrying rollers for actuating the cams for effecting pumping by causing the pusher plates to alternately contact their respective first or second means.

2. A pump arrangement in accordance with claim 1, wherein said guide means includes a rod of variable length.

3. A pump arrangement in accordance with claim 1 wherein said first and second means for separating includes first and second diaphragms wherein the guide means includes a rod aligned along said axis and affixed at the ends thereof to said pusher plates, wherein said diaphragms are not affixed to said pusher plates.

4. A pump arrangement comprising: first second and third chambers separated by first and second diaphragms respectively, said diaphragms defining said second chamber therebetween; first and second pusher plates, proximately contactable against the diaphragms, for pushing the diaphragms along an axis; and means for moving each of said pusher plates along said axis, wherein the pusher plates of the two pump diaphragms are connected together with a variable length guide means, and the means for moving includes a rotary electric motor mounted on said guide means and having a rotor carrying rollers which move the pusher plates by alternately actuating cam means carried on each of the pusher plates, to effectuate pumping.

5. A pump arrangement in accordance with claim 4 in which said rotary electric motor comprises a commutatorless assembly.

6. A pump arrangement in accordance with claim 1 wherein the guide means is aligned with said axis and connecting said pusher plates.

7. A pump arrangement in accordance with claim 4 wherein each of said first and third chambers includes entrance and exit conduits and means for connecting said entrance and exit conduits of the first chamber with a first blood circulating path and said entrance and exit conduits of the third chamber with a second blood circulating path.

8. A pump arrangement comprising first, second and third chambers separated by first and second means, said first and second means being adapted to be pushed along an axis in a manner to reduce the volumes in said first and third chambers, respectively, means for pushing said first and second means housed within said second chamber wherein the means for pushing includes first and second pusher plates for pushing the first and second means, the pusher plates being connected together with a variable length guide means, such means for pushing further including a rotary electric motor mounted on the guide means and having a rotor carrying rollers which move the pusher plates by alternately actuating cam means carried on each of the pusher plates to effectuate pumping wherein each of said first and third chambers includes entrance and exit conduits and means for connecting said entrance and exit conduits of said first chamber with a first blood circulating path and said entrance and exit conduits of said third chamber with a second blood circulating path.

9. An implantable artificial heart pump having a housing such pump further comprising:
   first and second sets of inlet and outlet valves;

first and second diaphragms separating the housing into a first chamber communicating with the first set of inlet and outlet valves, a second chamber communicating with the second set of inlet and outlet valves, and an intermediate chamber located between the first and second chambers;

drive means located in the intermediate chamber, for alternately contacting and pushing against the first and then the second diaphragms so as to expel fluid from the first and then the second chambers respectively, wherein the diaphragms are not connected to the drive means, and the intermediate chamber is part of a closed volume, so that each chamber is caused to refill with fluid from its inlet valve solely by the fluid pressure at the inlet and by the restoring suction on its diaphragm due to the change in volume of the intermediate chamber caused by pushing of the other diaphragm, wherein the drive means includes first and second pusher plates for pushing the first and second diaphragms, the pusher plates being connected together with a variable length guide means, such drive means further including a rotary electric motor mounted on the guide means and having a rotor carrying rollers which move the pusher plates by alternately actuating cam means carried on each of the pusher plates to effectuate pumping.

* * * * *